United States Patent [19]

Kehayias et al.

[11] Patent Number: 4,893,627

[45] Date of Patent: Jan. 16, 1990

[54] METHOD FOR NUCLEAR MAGNETIC RESONANCE IMAGING USING DEUTERUM AS A CONTRAST AGENT

[75] Inventors: Joseph J. Kehayias, Chestnut Hill, Mass.; Darrel D. Joel, Setauket, N.Y.; William H. Adams, Eastport, N.Y.; Harry L. Stein, Glen Head, N.Y.

[73] Assignee: The United States of America as represented by the United States Department of Energy, Washington, D.C.

[21] Appl. No.: 200,811

[22] Filed: May 26, 1988

[51] Int. Cl.[4] ............................................. A61B 5/05
[52] U.S. Cl. .......................................... 128/654; 424/9
[58] Field of Search ............... 128/653, 654; 324/307, 324/309; 424/9

[56] References Cited

U.S. PATENT DOCUMENTS

| | | | |
|---|---|---|---|
| 3,576,994 | 5/1971 | Parks et al. | 128/654 |
| 4,070,611 | 1/1978 | Ernst | 324/309 |
| 4,523,596 | 6/1985 | Macovski | 128/653 |
| 4,586,511 | 5/1986 | Clark, Jr. | 128/654 |
| 4,746,507 | 5/1988 | Quag | 424/9 |

OTHER PUBLICATIONS

American Journal of Clinical Nutrition, 1987, 45:1–6, copyrighted by American Society of Clinical Nutrition.

Primary Examiner—Ruth S. Smith
Assistant Examiner—John D. Zele
Attorney, Agent, or Firm—Vale P. Myles; James W. Weinberger; William R. Moser

[57] ABSTRACT

A method for in vivo NMR imaging of the blood vessels and organs of a patient characterized by using a dark dye-like imaging substance consisting essentially of a stable, high-purity concentration of $D_2O$ in a solution with water.

2 Claims, No Drawings

METHOD FOR NUCLEAR MAGNETIC RESONANCE IMAGING USING DEUTERUM AS A CONTRAST AGENT

The U.S. Government has rights in this invention pursuant to Contract Number DE-AC02-76CH00016, between the U.S. Department of Energy and Associated Universities, Inc.

The invention relates to a method for in vivo nuclear magnetic resonance (NMR) in which an image enhancing solution is injected into the patient and, more particularly relates to the use of deuterium oxide mixed with water to form such an image enhancing solution.

BACKGROUND OF THE INVENTION

It is well known that heavy water or deuterium oxide ($D_2O$, or $2H_2O$) is useful in nuclear magnetic resonance (NMR) spectrographic studies, such as those now widely used in biochemical research and in developing new applications for clinical research. An example of such prior art usage is in the measurement of total body water as it is associated with evaluations of acute and chronic alterations in hydration that can be caused by a variety of illnesses. In such methodology, the NMR signal of $D_2O$, or of a $D_2O/H_2O$ solution, appears at a frequency that is distinctly different from all other frequencies of deuterium belonging to any molecular fragment, therefore an accurate estimation of $D_2O$ in biological fluids is permitted. Such NMR spectroscopy methods are not, however, useful in providing in vivo NMR imaging of blood vessels and organs such as the heart, kidneys, liver, etc. of a patient.

There have been a number of earlier studies of the affect of heavy water on mammals. Theose studies involve either the ingestion of heavy water by the mammals, or occasionally a subcutaneous injection of heavy water into animals has been analyzed. So far as the present inventors are aware, those earlier studies did not involve any use of NMR imaging in connection with the ingestion or injection of heavy water into a living mammal patient.

In order to be useful for in vivo NMR imaging, a suitable imaging dye material must not resonate at the frequency of water hydrogen, and the dye material must not have an adverse affect on the patient's organs that are to be imaged with the method. In particular, the dye solution must be usable in a sufficient concentration for it to have a desirable level of effect on the NMR image. Thus, the use of solutions containing various radionuclides or other toxic substances are either severely limited or precluded from use as NMR imaging dyes for in vivo applications.

SUMMARY OF THE INVENTION

A method of in vivo nuclear magnetic resonance imaging is provided in which a stable, non-toxic deuterium isotope, in the form of $D_2O$, is used as a dye-like agent to enhance clinical NMR images of blood vessels and organs of a patient.

OBJECTS OF THE INVENTION

An object of the invention is to provide a method for in vivo NMR imaging of the vessels and organs of a patient by using an isosmotic solution of high purity $D_2O$ to act as a dye-like agent at the frequency of H-1 resonance when the solution is injected via a catheter into a blood vessel of a patient who is exposed to the magnetic field of an NMR system.

Another object of the invention is to provide an in vivo NMR imaging process that utilizes a non-toxic solution that appears as a dark dye-like agent when exposed to nuclear resonance.

A further object of the invention is to provide an in vivo NMR imaging method that uses a stable, radiation-free dye-like appearing imaging agent such as a suitably concentrated solution of high purity $D_2O$ (consisting of more than 99.0% by weight $D_2O$).

Further objects and advantages of the invention will become apparent to those skilled in the art from the description of it that follows.

DETAILED DESCRIPTION OF THE INVENTION

In a preferred form of the present invention, a NMR imaging dye-like agent (sometimes called a contrast agent) is prepared for in vivo injection into a patient whose blood vessels or organs are to be analyzed. It has been found that in order to produce a suitably dark NMR image, an isosmotic solution of high purity $D_2O$ and water, having a ratio of $D_2O/H_2O$ equal to at least 99.00% by weight $D_2O$ must be used in our method. We have found that the deuterium (D) nuclei emit no signal at the frequency of the H-1 resonance of an NMR system, accordingly, the $D_2O$ in our novel imaging agent appears as a dark dye when it is injected in vivo into a patient's blood vessel and exposed to the magnetic field of an NMR system. Thus, as blood circulates through the vessel and organs of a patient, the dye-like agent dilutes as it moves through the arteries into the organs, thereby affording clear NMR images that are useful in studying such flow and the related vessels and organs.

Because the $D_2O$ solution used in our method is free of tritium, and has no toxic effects, it can be safely used as a dye-like agent for in vivo imaging of blood vessels and organs. Accordingly, this method may replace the current use of radioisotopes such as Tl-201 and Tc-99m in various in vivo analyses, such as the assessment of the hypoperfused and necrotic myocardium and stress-related perfusion clinical examinations.

In practicing the method of the invention, the injection of the $D_2O$ solution is arranged to take place while a patient is located within the field of a NMR system magnet, so sequential H-1 images of the artery are thus immediately obtained. The solution may be injected into any suitable artery or vein of the patient in an acceptable amount of $D_2O$ to provide a desirably dark dye-like appearance of the $D_2O$ in the sequence of NMR images as the injected solution becomes diluted during its movement through the coronary arteries.

To the extent that the diluted solution is visible in the myocardium, kidneys and other organs, it is useful for making various studies of such organs. Relatively small doses of $D_2O$ have been found to constitute such acceptable amounts for forming a desirably dark dye-like NMR image. In one approach, an acceptable dosage of about 10 to 20 milliliters of high purity $D_2O$ in water solution can be injected into the coronary artery of a patient. In one experiment, a dosage of about 100 to 200 milliliters of high purity $D_2O$ (at least 99% by weight $D_2O$, in water) was injected into the renal artery of a dog and was found to provide a suitably dark NMR image. That volume is relatively small compared to the total body water volume of a typical patient. That fact and the fact that the $D_2O$ solution is made isotonic prior to its injection, results in the solution being found to exhibit no toxicity relative to the patient.

A typical hospital type NMR system can be used to practice the method of the invention. For example, the 0.6 Tesla Technicare system located at North Shore Hospital in Manhasset, Long Island, N.Y. has been found to be suitable for practicing the method of the invention. Another example of such a suitable system is the 1.5 Tesla GE system installed at Cedar Sinai Medical Center in Los Angeles, Calif.

EXAMPLE

An isosmotic solution of high purity $D_2O$ (about 99.81% by weight $D_2O$, in $H_2O$) was injected via a femoral catheter into the renal artery of an anesthetized dog while sequential H-1 images from a conventional (0.6 Tesla) NMR imaging system were obtained. Because the D nuclei in the solution emitted no signal at the frequency of the H-1 resonance, the $D_2O$ was found to appear as a "dark dye" as it moved through the artery, undergoing dilution, when it proceeded into the kidney. This test showed clear images of the artery, the progressive dilution of the $D_2O$ solution, and of the flow of the solution through the kidney.

We claim:

1. A method for in vivo NMR imaging consisting of positioning a patient within the magnetic field of an energized NMR system, administering an acceptable NMR imaging amount of stable, high-purity $D_2O$ in isosmotic water solution by injecting the solution through a catheter into a blood vessel of the patient, said acceptable amount of $D_2O$ being sufficient to enable the administered $D_2O$ to form dark dye-like images as the solution is subjected to the H-1 resonance of the system, said H-1 resonance being effected at a frequency at which $D_2O$ will not resonate, detecting H-1 resonance signals, and processing said signals to provide an image.

2. An NMR imaging method comprising using a dense solution of $D_2O$ and $H_2O$ as an imaging dye said dense solution of $D_2O$ and $H_2O$ having a ratio of $D_2O/H_2O$ equal to at least 99.00% by weight $D_2O$, causing H-1 resonance, detecting H-1 resonance signals, and processing said signals to provide an image.

* * * * *